(12) United States Patent
Borgstahl et al.

(10) Patent No.: US 7,466,798 B2
(45) Date of Patent: Dec. 16, 2008

(54) DIGITAL X-RAY CAMERA FOR QUALITY EVALUATION THREE-DIMENSIONAL TOPOGRAPHIC RECONSTRUCTION OF SINGLE CRYSTALS OF BIOLOGICAL MACROMOLECULES

(75) Inventors: Gloria Borgstahl, Omaha, NE (US); Jeff Lovelace, Omaha, NE (US); Edward Holmes Snell, Ardmore, AL (US); Henry Bellamy, Baton Rouge, LA (US)

(73) Assignee: Regents of the University of Nebraska, Board of Varner Hall, Omaha, NE (US)

( * ) Notice: Subject to any disclaimer, the term of this patent is extended or adjusted under 35 U.S.C. 154(b) by 253 days.

(21) Appl. No.: 11/278,738

(22) Filed: Apr. 5, 2006

(65) Prior Publication Data

US 2006/0259245 A1 Nov. 16, 2006

Related U.S. Application Data

(63) Continuation-in-part of application No. 10/681,874, filed on Oct. 7, 2003, now abandoned.

(51) Int. Cl.
*G01N 23/207* (2006.01)
(52) U.S. Cl. .................................. 378/74; 378/98.8
(58) Field of Classification Search ............. 378/71–81, 378/98.8
See application file for complete search history.

(56) References Cited

U.S. PATENT DOCUMENTS

| | | | |
|---|---|---|---|
| 3,866,067 A | 2/1975 | Amelio | |
| 5,978,444 A | 11/1999 | Atac | |
| 5,987,095 A | 11/1999 | Chapman | |
| 6,385,289 B1 | 5/2002 | Kikuchi | 378/79 |
| 6,468,346 B2 | 10/2002 | Arnowitz et al. | 117/68 |
| 6,498,829 B1 | 12/2002 | Borgstahl et al. | 378/73 |
| 6,782,076 B2 | 8/2004 | Bowen | |

FOREIGN PATENT DOCUMENTS

WO 03/040361 5/2003

OTHER PUBLICATIONS

Bellamy et al., "The high-mosaicity illusion:revealing the true physical characteristics of macromolecular crystals", Acta Cryst. 2000 D56:986-995.
Boggon et al., "Synchrotron X-ray reciprocal-space mapping, topography and diffraction resolution studies of macromolecular crystal quality", Acta Cryst. 2000 D56:868-880.

(Continued)

*Primary Examiner*—Jurie Yun
(74) *Attorney, Agent, or Firm*—Niels Haun; Dann Dorfman Herrall & Skillman, PC

(57) ABSTRACT

The present invention provides a digital topography imaging system for determining the crystalline structure of a biological macromolecule, wherein the system employs a charge coupled device (CCD) camera with antiblooming circuitry to directly convert x-ray signals to electrical signals without the use of phosphor and measures reflection profiles from the x-ray emitting source after x-rays are passed through a sample. Methods for using said system are also provided.

4 Claims, 1 Drawing Sheet

OTHER PUBLICATIONS

Dobrianov et al., "X-ray Topographic Studies of Protein Crystal Perfection and Growth", Acta Cryst. 1998 D54:922-937.

Ludwig et al., "Three-dimensional imaging of crystal defects by 'topography'", J. Appl. Cryst. 2001 34:602-607.

Otalora et al., "Topography and high resolution diffraction studies in tetragonal lysozyme", Journal of Crystal Growth 1999 196:546-558.

Stojanoff et al., "X-ray Topography of Tetragonal Lysozyme Grown by the Temperature-Controlled Technique", Acta Cryst. 1997 D53:558-595.

Stojanoff et al., "X-ray topography of a lysozyme crystal", Acta Cryst. 1996 A52:498-499.

Vetter et al., "Synchrotron white-beam X-ray topography of ribonuclease S crystals", Acta Cryst. 2002 D58:579-584.

Baruchel, J., et al., "Present State and Perspectives of Synchrotron Radiation Diffraction Imaging," J. Synchrotron Rad., 9:107-114, 2002.

Charron, C., et al., "Crystallization in the Presence of Glycerol Displaces Water Molecules in the Structure of Thaumatin," Acta Cryst., D58:2060-2065, 2002.

Lovelace, J.J., et al., "Advances in Digital Topography for Characterizing Imperfections in Protein Crystals," Appl. Cryst., 38:512-519, 2005.

DIGITAL X-RAY CAMERA FOR QUALITY EVALUATION THREE-DIMENSIONAL TOPOGRAPHIC RECONSTRUCTION OF SINGLE CRYSTALS OF BIOLOGICAL MACROMOLECULES

This application is a continuation-in-part of U.S. patent application Ser. No. 10/681,874 filed Oct. 7, 2003 now abandoned, incorporated herein by reference in its entirety.

Pursuant to 35 U.S.C. 202 (c) it is hereby acknowledged that the United States Government has certain rights in the invention described herein, which was made in part with federal funds from NASA Grant No. NAG8-1825.

BACKGROUND OF THE INVENTION

X-ray topography is a well-known method for characterizing the microstructure of single crystals. It uses x-ray diffraction to measure defects and imperfections in crystal structures. A defect in crystalline structure affects how well the protein structure can be determined. Many of the basic macromolecules of organisms, e.g. proteins, DNA, RNA, can be crystallized. A defect in protein structure may affect the function of that protein, possibly resulting in disease.

There are currently many x-ray topography devices and methods of identifying defects in crystals using white beam or monochromatic x-ray topographs. The white beam technique (Laue geometry) provides rapid imaging but results in low effective resolution. Protein crystals tend to suffer severe and rapid degradation from the intensity of a white synchrotron beam. However, this technique is useful for rapidly screening samples. Monochromatic beam methods can provide more detailed information but require careful alignment and longer exposures. (Stojanoff, et al. (1996) *Acta Cryst.* A52:498-499; Stojanoff, et al. (1997) *Acta Cryst.* D53:588-595; Vetter, et al. (2002) *Acta Cryst.* D58:579-584; Boggon, et al. (2000) *Acta Cryst.* D56:868-880).

U.S. Pat. No. 6,385,289 (Kikuchi) teaches a device using two-dimensional information of x-ray intensities and a charge coupled device (CCD) camera with larger pixels (12 or 24 μm) than the present invention (less than 10 μm, preferably 8 μm) as described for x-ray topography. The device measures x-ray rocking curves using a movable x-ray detector which measures x-ray intensities diffracted off of the surface of a sample. Kikuchi's method diffracts x-rays off of a surface and measures the angle of the diffraction and the intensity of the x-rays when they strike the surface of an x-ray detector. In contrast, the present invention uses transmission geometry, where the x-rays are diffracted by passing through a sample.

U.S. Pat. No. 6,468,346 (Arnowitz et al.) teaches a method of improving crystal growth using magnetic fields or varying levels of gravity. Both earth and space-grown crystal samples were studied. The space-grown crystals were found to exhibit higher crystallographic perfection. X-ray topographic images are used to reveal defects in the crystals and to permit identification of the sets of conditions that produce crystals having the fewest defects. A method to generate topographic images is not taught.

Japanese patent 2000314708 teaches an x-ray topography apparatus with a movable stand, x-ray source and irradiation side slits which regulate x-rays from the x-ray source toward a specimen. The radiation side split is arranged between the specimen and a CCD sensor that detects x-rays from the specimen. A specimen support frame holds the specimen while it is measured.

U.S. Pat. No. 6,498,829 (Borgstahl et al.) teaches a method for mosaic spread analysis which uses super fine Φ-slicing data collection, unfocused monochromatic radiation and a suitable fast readable area detector such as a CCD. Random radiation events in the phosphor or optical taper intensities are removed from the diffraction data to create reflection profiles.

Most CCD systems presently used for crystallography have a fiber optic bundle in front of the CCD relative to the x-rays. The fiber optic bundle is generally tapered like a cone with the small end at the CCD. This provides a detecting area larger than the CCD chip. A phosphor is required because the fiber optic bundle is unable to transmit x-rays. The phosphor converts the x-rays into visible light. The fiber optic bundle also helps to protect the CCD from the damaging x-rays by absorbing the rays that are not converted by the phosphor into visible light. The fiber optic bundle has the disadvantage of reducing the spatial resolution of the CCD.

There is a need for a topography system that is low cost, rapid, quantitative and directly reads out to electronic media. Traditionally, single crystal topography was employed using x-ray film or nuclear emulsion plates. The currently available technology has some disadvantages, including long exposure times, slow sampling rate and chemical processes that can vary according to the protocol used, and the age of the reagents used. The present invention overcomes these problems by using a digital camera, giving the user real-time imaging, minimizing exposure times, and eliminating the variable chemical processes used by conventional methods.

SUMMARY OF THE INVENTION

The present invention provides a digital topography imaging system for a biological macromolecule comprising an x-ray emitting source which comprises a shutter; a sample holder adapted to hold a sample comprising at least one biological macromolecule; positioning systems for the camera and the sample holder; a charge coupled device (CCD) camera which measures reflection profiles from the x-ray emitting source; a means for controlling pixel image corruption due to pixel overloading in the CCD camera; and a means for acquiring and displaying images of the sample.

The digital topography imaging system of the present invention may be employed to determine crystalline structure of a biological macromolecule.

DETAILED DESCRIPTION OF THE INVENTION

Figure 1:
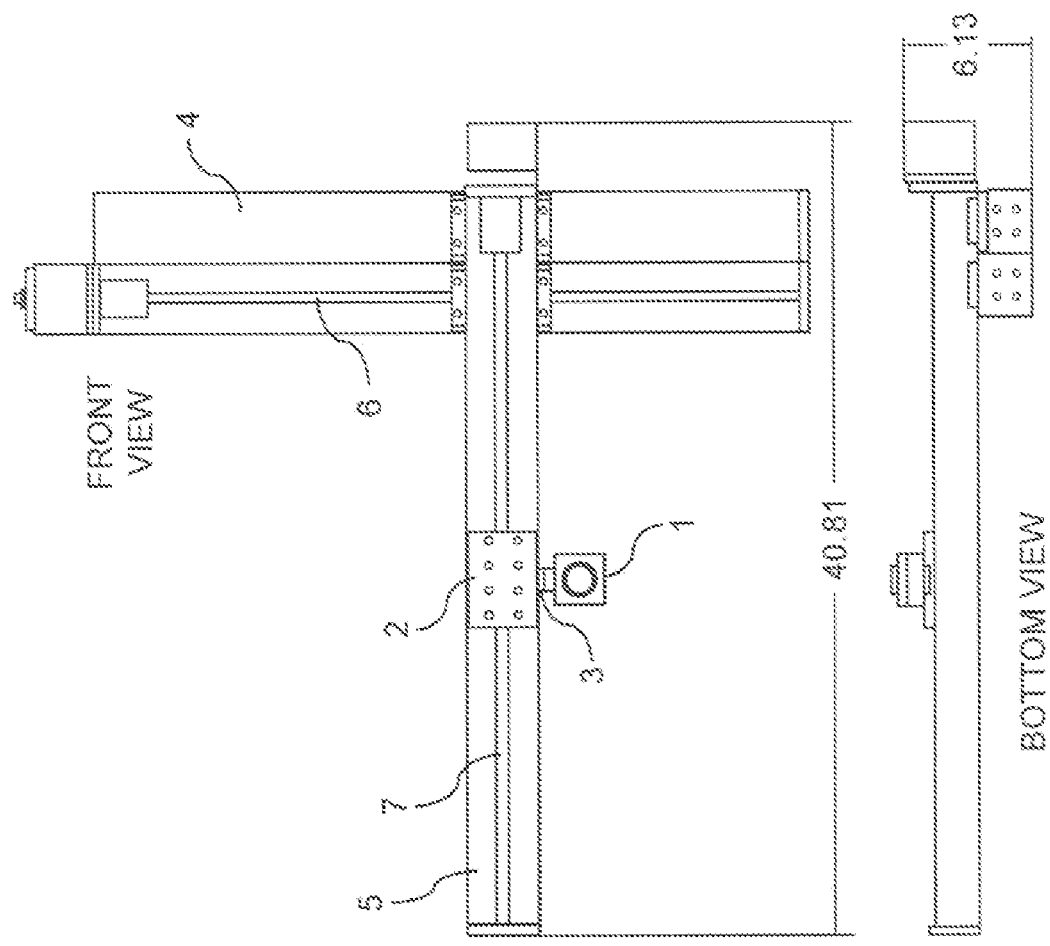
FIG. 1 shows the system assembly of the present invention.
Figure 1:
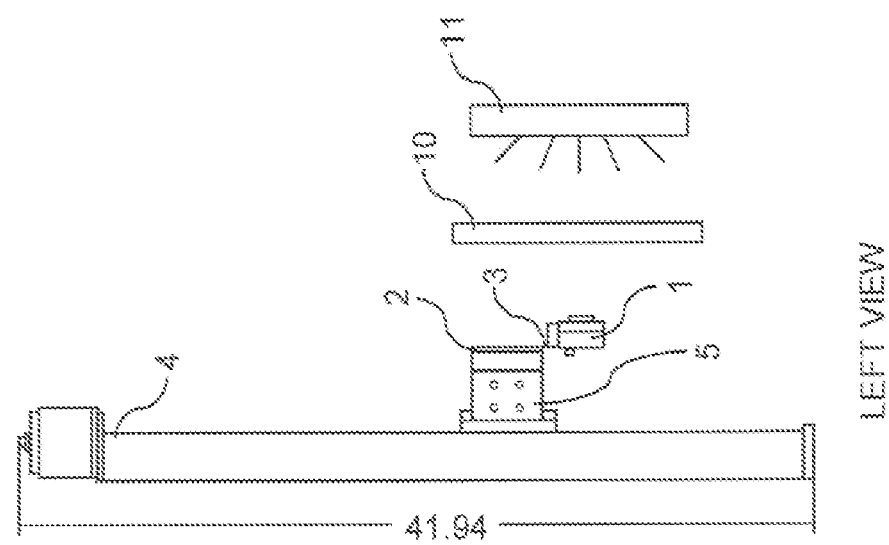

Topography is the high spatial resolution imaging of the individual parts of a crystal contributing to an X-ray reflection. (Otálora, et al. (1999) *J. Cryst. Growth* 196:546-558). Topography provides insight into the internal diffraction properties of a crystal (Stojanoff, et al. (1996) supra; Stojanoff, et al. (1996) *Synchotron Radiation News* 9:25-26; Stojanoff, et al. (1997) supra; Dobrianov, et al. (1998) *Acta Cryst.* D54:922-937; Otálora, et al. (1999) supra; Boggon et al. (2000) supra). The lattice deformations surrounding defects within the crystal produce the contrast in the topographic image. By quantifying these data, one can compare the quality of different crystals.

Typically, images are acquired with a fine-grain x-ray-sensitive film or nuclear emulsion plates. The fine grain size (typically 2-3 μm with film and down to 1 μm with nuclear emulsion) has been the sole reason film and nuclear emulsion plates have been utilized for so long in X-ray topography.

Drawbacks to using film include slow processing time, variation between batches of film and processing chemicals, and a limited dynamic range. Repeatable, high accuracy, quantitative analysis with film-based techniques is different.

These problems arise because the film must be digitized before a computer can process the data. As part of the digitization process, the frames must be geometrically corrected and registered with one another. Even with fiducial marks, this process can be time consuming. Film-based processes are slowly being replaced with digital equivalents in many fields.

The present invention uses a CCD to capture digital topography images of biological macromolecules directly. Some benefits of using a CCD are that it is extremely fast, can be very sensitive, and the data are automatically digitized and registered. However, the spatial resolution is normally not as high as film, and dark current limits the exposure time of the system. This problem is minimized by lowering the operating temperature of the CCD.

There are tradeoffs in the design of a CCD chip. For example, if the pixel size is reduced to increase the spatial resolution, the electron well capacity is reduced, which also reduces the dynamic range.

For use in topography, spatial resolution is the most important parameter. Therefore, a CCD with small pixel size (e.g., 8 μm) was selected for the present invention. In a previous study, a CCD-based x-ray camera was used to study topography of synthetic diamonds. (Ludwig, et al. (2000) *J. Appl. Cryst.* 34:602-607). However, Ludwig, et al. used the CCD with a powder phosphor to convert the x-rays to visible light and a fiber-optic faceplate to channel the visible light to the chip surface for detection.

The present invention uses the relatively weak diffraction of biological macromolecular crystals and direct detection of x-rays by the CCD chip. The CCD chip used in the present invention incorporates anti-blooming circuitry. With anti-blooming circuits, spatial resolution is preserved and intensity information is lost in pixels which overflow. The preservation of spatial resolution is very useful for topography.

The present invention comprises a low cost, real-time digital topography imaging system for evaluation of three-dimensional topographic reconstruction of single crystals of biological macromolecules such as proteins, peptides, DNA, and RNA, thereby replacing x-ray film and nuclear emulsion plates. The present invention uses a CCD camera with a very fine pixel size to convert x-rays into an electrical signal.

The imaging system directly converts x-rays to an image without the use of phosphor. The CCD camera of the imaging system is designed for short exposure applications of less than one second and therefore has a relatively high dark current leading to noisy, raw images. The resulting noisy, raw images are then processed to sharpen them, providing a clearer image of the data.

The digital topography imaging system of the present invention comprises an x-ray emitting source; a sample holder adapted to hold a sample containing a biological macromolecule; a charge coupled device (CCD) camera with antiblooming circuitry which reduces pixel image corruption due to CCD camera pixel overloading; positioning systems for the camera and the sample holder; and a means for acquiring and displaying images of biological macromolecule crystals that have been processed for clarity.

the x-ray emitting source further comprises a shutter, allowing for variable exposure times. The x-ray emitting source must provide x-rays that are nearly parallel and have a bandwidth of less than 1%. The x-ray beam must be larger enough to cover all of the biological sample, or the region of the sample that is of interest. Exposure time is dependent on the strength of the source and the nature of the sample. The method of the present invention can be used with exposure times of any length.

The sample holder can be any suitable size or material compatible with crystals of biological macromolecules. The sample holder is preferably moveable so that the sample can be positioned in the line of the x-ray beam. The holder must not translate or allow the sample to vibrate during data collection. The sample holder is rotated. Movements of the sample holder may be computer controlled. In the present invention, a positioning system controls the CCD camera. The camera positioning system may also be computer controlled.

The CCD chips used in most crystallographic applications are expensive, so the protection offered by the fiber optic bundle is necessary. The CCD chip used in the present invention is inexpensive, when compared to the chips used in other applications. The CCD of the present invention does not require protection from x-ray damage. The intensity of the x-ray striking the surface of the CCD, in the present invention, is reduced because the x-ray beams are diffracted by the biological sample prior hitting the CCD.

The charge coupled device (CCD) camera measures reflection profiles from the x-ray emitting source. To acquire an image which can be used to determine the crystalline structure of biological macromolecules, particular embodiments embrace a CCD camera with a very fine pixel size of 10 μm or smaller. While an 8 μm pixel size was used in one embodiment, pixel sizes in the range 0.05 μm to 10 μm are suitable with pixel sizes less than 5 μm particular useful for analyzing the structure of biological macromolecules. Using the CCD camera with antiblooming circuitry allows for accurate measurement of a very bright pixel next to a very dim pixel and the high spatial resolution provides a detailed image of the reflection.

Antiblooming circuitry is used as a means for controlling pixel image corruption due to CCD pixel overloading (blooming). Blooming occurs in a CCD when the charge accumulating in a pixel spills over into neighboring pixels. The result is a strong signal in one pixel, appearing as a large spot. Such a large spot may occupy any pixels and drown out weaker signals in the neighboring pixels. Antiblooming circuitry provides sharp detail between regions of the crystal, even when neighboring pixels are overloaded.

After an exposure, an image of the sample is captured from the CCD camera directly to memory in a computer. The time it required for the data from the CCD to transfer to computer memory is known as "read out time" and is typically much less than a second. As each pixel is transferred from the CCD to memory, the electrical charge accumulated in the CCD for each individual pixel is converted to an integer value. The actual range of values is dependent on the resolution of the analog to digital converter (ADC). This resolution is measured in bits with a typical ADC having a resolution between 8 and 16 bits. The ADC is part of the computer interface card that connects the CCD camera to a computer system and is commercially available.

A computer program assigns a color to each value for each pixel. Pixels with the same value receive the same color as defined in the color map. A color image of the sample is displayed on a screen. The color image represents the intensity measured for each pixel. The image may be scaled to fit the screen.

In one embodiment, a method for digital topography imaging comprises placing a biological sample in the sample holder of the digital topography system of the present invention, positioning the sample holder between the x-ray emitting source and the CCD camera, exposing the sample to x-rays from the x-ray emitting source, measuring the x-ray reflection angles of the x-rays that are passed through the sample from the x-ray emitting source with the CCD camera to form a raw image, and processing the raw image measured by the CCD camera with a computer program which provides clearer images of the structure of the biological sample, and displaying those images on a screen.

In another embodiment, the raw image produced using the above method is processed using a multi step method to remove the background and system noise. The first step is to remove the dark current noise by subtracting a dark current image of equal exposure. Any electric ripple noise is removed using a wavelet transform. The wavelet transform comprises four filters; a low frequency decomposition filter, a high frequency decomposition filter, a low frequency reconstruction filter, and a high frequency reconstruction filter. Then, a histogram cut-off filter is used to reduce the remaining background noise. A median filter is used to clean up the speckled nature of the data. A wavelet transform is used to enhance resolution. A histogram filter is used to filter out any remaining low level noise. The data is then expanded and digitized into an integer range of 0-255. A color table having assigned colors for each numerical value is created with the integer value to determine how effective the processing eliminated noise from the data. For example, a value of zero is white. Values of 1-255 progress incrementally from blue to red. Results having an integer value close to zero in the background region are desired.

After processing, animations are constructed with the corresponding reflection profile to provide the diffraction of the crystal volume versus the oscillation angle, as well as composite images depicting parts of the crystal of the biological macromolecule.

the present invention preferably uses a two-dimensional positioner to place the CCD camera and its holder into the x-rays emitted from the source or diffracted form the sample. The positioning system used in the present invention may be created by connecting two Velmex BiSlides™ together at right angles to each other. Positioning products from other vendors are also acceptable for use.

As shown in FIG. 1, in a preferred embodiment, the system assembly of the present invention comprises a base with an inlaid screw, placed on a horizontal flat surface. The horizontal BiSlide 5 is mounted to the vertical BiSlide 4. The vertical screw 6 allows the horizontal BiSlide 5 to move up and down the length of the vertical BiSlide 4, relative to the horizontal flat surface. The camera 1 is mounted to the horizontal BiSlide 5 by the mounting bracket 2 and the camera mounting bracket 3. The horizontal BiSlide 5 has an inlaid screw allowing the mounting bracket 2, camera mounting bracket 3, and camera 1 assembly to move laterally along the length of the horizontal BiSlide 5. Both the vertical and horizontal screw assemblies 6, 7 allow the camera 1 to be positioned where needed on the sample holder 10 located in front of the x-ray emitting source 11 when the topography imaging system of the present invention is used.

The topography imaging system of the present invention may be mounted onto a software controlled, x-y-2θ positioning stage that can be positioned in front of a QUANTUM4™ CCD detector for the collection of topographs. For example, the QUANTUM4™ is used for measuring the intensity of hundreds of reflections simultaneously. It measures the integrated intensity of the reflections, but does not provide data on the internal structure of the reflection. In the present invention, the CCD detector is used to locate diffracted beams in terms of x position, y position and angular range from the crystal over a large area. The CCD camera is then used to collect high spatial resolution topography on the individual beams.

Although topographs will only be measured in the vertical orientation, the horizontal axis will be used to center the reflection in the detector and to compensate for spot movement as the reflection passes through Ewald's sphere.

The present invention is further illustrated in the following, non-limiting examples.

EXAMPLE 1

The CCD topography system is based on an Electrim Corporation EDC-2000S camera which uses a Texas Instruments TI-TC281 CCD chip. For this experiment, Texas Instruments provided a TI-TX281-31 CCD, which was a TC281 with the cover glass removed.

The TC281 has an 8×8 mm active area consisting of a 1000×1000 array of 8 μm square pixels. The pixel well capacity is 32,000 electrons. The CCD contains special anti-blooming circuitry. EDC-2000S offers software-programmable adjustment of the gain, offset, and exposure time.

NSLS Beamline X26-C was used for this experiment. It was configured for unfocused monochromatic radiation at 1.52 Å. The assignments of the motor axes differ from conventional Eulerian cradle geometries typically used.

In an effort to simulate a conventional setup, the $\omega$ axis was held stationary so that the $\psi$ axis was held perpendicular to the x-ray beam. The axis $\phi$ the $\chi$ were used to position the reflections so that they were directly above the beam in order to minimize the effect of beam divergence and Lorentz broadening on the reflection profile (Bellamy, et al. (2000) *Acta Cryst.* D56:986-995). The 2θ and ν motions were used to position the detectors. After a reflection was located with the scintillation counter, the topography camera was inserted in front of the scintillation counter and held in place with custom-sized length of clear reusable single-sided bonding strip. The camera and the x-ray shutter were synchronized manually; the camera exposure was 10 seconds and the x-ray shutter time was 5 seconds.

The image were recorded using a software package. The images are written to disk in TIFF format (Aldus Corporation 1986), which allows image-processing concepts to be prototyped and analyzed with MATLAB (The Math Works Inc. 1992).

The raw data images from the camera were quite noisy and were passed through a seven step processing sequence to improve the images. The first step was to remove the dark current noise by subtracting a dark-current (no x-rays) image of equal exposure time. The TC-281 CCD was designed for use in short exposure time environments (<<1 second) and has a significant dark current when the exposure time is on the order of seconds, as it was in this case.

The second step was to remove the electrical ripple noise that was present over the entire surface of the CCD. The wavelet transform was used to reduce the ripple noise. The wavelet transform provides several advantages over the Fourier transform for manipulating images (Mallat (1998) "A Wavelet Tour of Signal Processing"). The two most important were that all of the coefficients were real and that frequency information was localized. The wavelet transform consisted of four filters derived from a scaling function and a related wavelet function. These filters form orthonormal basis functions in the filtering space in much the same way that sine and cosine form basis functions in Fourier space. Decomposition low-pass filter (L), a decomposition high pass filter (H), a reconstruction low pass filter and a reconstruction high pass filter were used. A wavelet coefficient was calculated by taking the dot product of the filter with a group of pixel values. The filter was indexed across the image two pixels at a time, and a coefficient was calculated at each location (Strang and Nguyen (1996) "Wavelets and Filter Banks"). For a two-dimensional image, the filters were first applied along the horizontal direction and then along the vertical direction leading to a two-letter convention that described the filter process.

A channel labeled LH indicated that the L filter was applied along the horizontal followed by the H filter along the vertical. For an image at the first stage of decomposition there were four channels named LL, LH, HL and HH. The decomposition channels each contained ¼ the number of pixels in the original image so that the total number of pixels remained unchanged after the transform was applied.

When shown on an image, the upper left was normally LL, upper right was LH, lower left was HL and lower right was HH. A channel can undergo a further decomposition and the resulting sub-channels follow the same convention. When the image was decomposed with a sixth order Daubechies wavelet (Daubechies (1992) "Ten Lectures on Wavelets") most of the complex noise appeared in the coefficients of the LH channels.

To reduce the complex noise, a one level decomposition was performed followed by a reconstruction with LH decomposition removed. The resulting image has a more evenly distributed background with lower overall intensity and less structure.

For the third step, a histogram cut-off filter was used to remove the remaining background noise from the image and leave the intensity near the reflection. The histogram filter found the average and standard deviation of all pixels and then set each pixel with a value less than the mean, plus 2.5 standard deviations to zero. The fourth step was to apply a median filter to clean up the speckled nature of the data. The median filter replaces the value of each pixel with the median value of a box of surrounding pixels.

The fifth step was to use the wavelet transform to enhance the resolution to roughly 4×4 µm. To enhance the resolution, the image form the fourth step was submitted to the inverse wavelet transform as the LL decomposition. The other three channels were set to zero. The resulting reconstruction had double the resolution. This approach was reasonable because in most wavelet decompositions the majority of the signal, in terms of total energy, was contained in the LL channel. The sixth step was to use a histogram cut off filter and clean out any remaining low-level noise. The method of step 4 was used.

The seventh step was to expand and digitize the data back into the integer range 0 to 255, by examining the entire sequence and using the maximum and minimum values to scale all the images in the sequence. The color table used in all of the reflection images had level zero as white and then levels 1 through 255 going from blue to red, respectively. Using white as level zero showed how well the processing was able to eliminate the noise from the data.

EXAMPLE 2

Sequences of topographic images were collected on two different reflections form a large cubic-insulin crystal (>500× 500 µm). The sequences were collected as a series of stills about the $\psi$ axis.

Image sequences for Crystal A were taken. The image sequences from Crystal A revealed an area of the crystal that stayed in diffracting condition for a longer amount of time in all images. The second reflection form Crystal A appeared to be composed of three large diffracting areas, two smaller ones on the right side of the crystal, and a larger one on the left side. There was a small gap of almost no diffraction dividing those areas.

Comparison of the Crystal A image sequences for reflections 1 and 2 showed that images were significantly degraded between reflection 1 and reflection 2. Reflection 2 yielded an image that was speckled and of a lower intensity. Possible reasons for this degradation included radiation damage, dehydration, and the possibility that this reflection would normally have a weaker intensity.

EXAMPLE 3

Sequences of topographic images were collected on four different reflections from a second large cubic-insulin crystal (>500×500 µm). The sequences were collected as a series of stills about the $\psi$ axis.

Crystal B was mounted and used exclusively for topography measurements. All measured reflections of Crystal B were well-defined and the signal was significantly above the background. The post-experimental picture of Crystal B showed no yellowing of the crystal, indicating that it suffered less radiation damage than Crystal A.

The images of Crystal B's topography showed it to be more complex than Crystal A. Crystal B had sharp transitions between areas of the crystal that were diffracting during the specimen rotation, rather than the smooth transitions seen during the rotation of Crystal A.

What is claimed is:

1. A method of digital topography imaging wherein raw images are computer processed using a multi step method comprising:
   a) placing a sample comprising at least one biological macromolecule in a sample holder adapted to hold a sample comprising at least one biological macromolecule;
   b) positioning the sample holder between an x-ray emitting source and a CCD camera;
   c) exposing the same sample to x-rays from the x-ray emitting source;
   d) measuring x-ray reflection angles of the x-rays that are passed through the sample from the x-ray emitting source with the CCD camera to form a raw image;
   e) processing the raw image measured by the CCD camera with a computer program to provide a clearer image of a crystal structure of the sample;
   f) subtracting a dark current image of equal exposure to remove dark current noise;
   g) removing electric ripple noise with a multiple filter wavelet transform;
   h) using a histogram cutoff filter to cut remaining background noise;
   i) using a median filter to clean speckle nature of the data;
   j) using a wavelet transform to enhance resolution;
   k) filtering remaining low level noise with a histogram filter; and l) digitizing the data into an integer range wherein each numerical value is associated with a corresponding color, so that clear images of the sample are displayed.

2. The method of claim 1 wherein the multiple filter wavelet transform comprises a low frequency decomposition filter, a high frequency decomposition filter, a low frequency reconstruction filter and high frequency reconstruction filter.

3. The method of claim 1 further comprising animating the processed images to show the diffraction of crystal volume versus the oscillation angle.

4. The method of claim 1 further comprising determining the crystalline structure of the sample.

* * * * *